US012161505B2

United States Patent
Glide-Hurst et al.

(10) Patent No.: US 12,161,505 B2
(45) Date of Patent: Dec. 10, 2024

(54) PATIENT INTERFACE SYSTEM

(71) Applicant: Delphinus Medical Technologies, Inc., Novi, MI (US)

(72) Inventors: Carri K. Glide-Hurst, Novi, MI (US); Nebojsa Duric, Novi, MI (US); Peter J. Littrup, Novi, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 1179 days.

(21) Appl. No.: 16/212,760

(22) Filed: Dec. 7, 2018

(65) Prior Publication Data

US 2019/0142367 A1    May 16, 2019

Related U.S. Application Data

(63) Continuation of application No. 14/486,551, filed on Sep. 15, 2014, now Pat. No. 10,201,324, which is a continuation-in-part of application No. 12/115,174, filed on May 5, 2008, now Pat. No. 8,870,771.

(60) Provisional application No. 60/915,946, filed on May 4, 2007.

(51) Int. Cl.
| | |
|---|---|
| *A61B 8/08* | (2006.01) |
| *A61B 8/00* | (2006.01) |
| *A61B 8/15* | (2006.01) |
| *A61B 5/00* | (2006.01) |

(52) U.S. Cl.
CPC ............ *A61B 8/0825* (2013.01); *A61B 8/085* (2013.01); *A61B 8/0858* (2013.01); *A61B 8/15* (2013.01); *A61B 8/406* (2013.01); *A61B 8/4494* (2013.01); *A61B 8/5223* (2013.01); *A61B 5/4312* (2013.01); *A61B 8/4281* (2013.01)

(58) Field of Classification Search
None
See application file for complete search history.

(56) References Cited

U.S. PATENT DOCUMENTS

| | | | |
|---|---|---|---|
| 3,154,067 A | 10/1964 | Stenstrom et al. |
| 3,771,355 A | 11/1973 | Sachs |
| 3,881,466 A | 5/1975 | Wilcox |

(Continued)

FOREIGN PATENT DOCUMENTS

| | | | |
|---|---|---|---|
| AU | 3443295 A | 5/1996 |
| CA | 2324602 A1 | 9/1999 |

(Continued)

OTHER PUBLICATIONS

Hayakawa, Y., Inada, T., Ueno, E., Aiyoshi, Y., Aoshima, N., Yosioka, K., & Wagai, T. (1985). Mass Screening of Breast Cancer by Ultrasound Transmission Technique—Theoretical Considerations. Japanese Journal of Applied Physics, 24(S1), 82. (Year: 1985).*

(Continued)

*Primary Examiner* — Christopher Koharski
*Assistant Examiner* — Renee C Langhals
(74) *Attorney, Agent, or Firm* — WILSON SONSINI GOODRICH & ROSATI

(57) ABSTRACT

A method for categorizing whole-breast density is disclosed. The method includes the steps of exposing breast tissue to an acoustic signal; measuring a distribution of an acoustic parameter by analyzing the acoustic signal; and obtaining a measure of whole-breast density from said measuring step. An apparatus is also disclosed.

12 Claims, 6 Drawing Sheets

(56) References Cited

U.S. PATENT DOCUMENTS

| | | |
|---|---|---|
| 3,886,489 A | 5/1975 | Jones |
| 3,925,610 A | 12/1975 | French et al. |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |
| 4,144,877 A | 3/1979 | Frei et al. |
| 4,222,274 A | 9/1980 | Johnson |
| 4,250,894 A | 2/1981 | Frei et al. |
| 4,317,369 A | 3/1982 | Johnson |
| 4,328,707 A | 5/1982 | Clement et al. |
| 4,363,326 A | 12/1982 | Kopel |
| 4,412,288 A | 10/1983 | Herman |
| 4,431,008 A | 2/1984 | Wanner et al. |
| 4,433,690 A | 2/1984 | Green et al. |
| 4,481,948 A | 11/1984 | Sole |
| 4,509,368 A | 4/1985 | Whiting et al. |
| 4,515,165 A | 5/1985 | Carroll |
| 4,541,436 A | 9/1985 | Hassler et al. |
| 4,542,744 A | 9/1985 | Barnes et al. |
| 4,562,540 A | 12/1985 | Devaney |
| 4,564,019 A | 1/1986 | Miwa |
| 4,606,342 A | 8/1986 | Zamba et al. |
| 4,646,756 A | 3/1987 | Watmough et al. |
| 4,662,222 A | 5/1987 | Johnson |
| 4,671,256 A | 6/1987 | Lemelson |
| 4,722,056 A | 1/1988 | Roberts et al. |
| 4,733,562 A | 3/1988 | Saugeon |
| 4,855,911 A | 8/1989 | Lele et al. |
| 4,858,124 A | 8/1989 | Lizzi et al. |
| 4,917,096 A | 4/1990 | Englehart et al. |
| 4,932,414 A | 6/1990 | Coleman et al. |
| 4,941,474 A | 7/1990 | Pratt, Jr. |
| 5,003,979 A | 4/1991 | Merickel et al. |
| 5,025,792 A | 6/1991 | Hon et al. |
| 5,029,476 A | 7/1991 | Metala et al. |
| RE33,672 E | 8/1991 | Miwa |
| 5,095,909 A | 3/1992 | Nakayama et al. |
| 5,103,129 A | 4/1992 | Slayton et al. |
| 5,143,069 A | 9/1992 | Kwon et al. |
| 5,158,071 A | 10/1992 | Umemura et al. |
| 5,158,536 A | 10/1992 | Sekins et al. |
| 5,178,147 A | 1/1993 | Ophir et al. |
| 5,179,455 A | 1/1993 | Garlick |
| 5,212,571 A | 5/1993 | Garlick et al. |
| 5,255,683 A | 10/1993 | Monaghan |
| 5,260,871 A | 11/1993 | Goldberg |
| 5,267,566 A | 12/1993 | Choucair et al. |
| 5,268,876 A | 12/1993 | Rachlin |
| 5,269,309 A | 12/1993 | Fort et al. |
| 5,280,788 A | 1/1994 | Janes et al. |
| 5,296,910 A | 3/1994 | Cole |
| 5,297,553 A | 3/1994 | Sliwa, Jr. et al. |
| 5,304,173 A | 4/1994 | Kittrell et al. |
| 5,305,752 A | 4/1994 | Spivey et al. |
| 5,318,028 A | 6/1994 | Mitchell et al. |
| 5,329,817 A | 7/1994 | Garlick et al. |
| 5,339,282 A | 8/1994 | Kuhn et al. |
| 5,349,954 A | 9/1994 | Tiemann et al. |
| 5,372,138 A | 12/1994 | Crowley et al. |
| 5,394,875 A | 3/1995 | Lewis et al. |
| 5,398,691 A | 3/1995 | Martin et al. |
| 5,413,108 A | 5/1995 | Alfano |
| 5,415,164 A | 5/1995 | Faupel et al. |
| 5,421,338 A | 6/1995 | Crowley et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,492,126 A | 2/1996 | Hennige et al. |
| 5,501,655 A | 3/1996 | Rolt et al. |
| 5,513,639 A | 5/1996 | Satomi et al. |
| 5,524,630 A | 6/1996 | Crowley |
| 5,546,945 A | 8/1996 | Soldner |
| 5,548,658 A | 8/1996 | Ring et al. |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,588,430 A | 12/1996 | Bova et al. |
| 5,590,653 A | 1/1997 | Aida et al. |
| 5,590,657 A | 1/1997 | Cain et al. |
| 5,596,992 A | 1/1997 | Haaland et al. |
| 5,606,971 A | 3/1997 | Sarvazyan |
| 5,609,152 A | 3/1997 | Pellegrino et al. |
| 5,620,479 A | 4/1997 | Diederich |
| 5,640,956 A | 6/1997 | Getzinger et al. |
| 5,643,179 A | 7/1997 | Fujimoto |
| 5,660,185 A | 8/1997 | Shmulewitz et al. |
| 5,664,573 A | 9/1997 | Shmulewitz |
| 5,673,698 A | 10/1997 | Okada et al. |
| 5,678,565 A | 10/1997 | Sarvazyan |
| 5,715,825 A | 2/1998 | Crowley |
| 5,722,411 A | 3/1998 | Suzuki et al. |
| 5,743,863 A | 4/1998 | Chapelon |
| 5,749,364 A | 5/1998 | Sliwa, Jr. et al. |
| 5,759,162 A | 6/1998 | Oppelt et al. |
| 5,762,066 A | 6/1998 | Law et al. |
| 5,766,129 A | 6/1998 | Mochizuki |
| 5,785,663 A | 7/1998 | Sarvazyan |
| 5,787,049 A | 7/1998 | Bates |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,830,133 A | 11/1998 | Osten et al. |
| 5,833,614 A | 11/1998 | Dodd et al. |
| 5,833,627 A | 11/1998 | Shmulewitz et al. |
| 5,833,633 A | 11/1998 | Sarvazyan |
| 5,833,634 A | 11/1998 | Laird et al. |
| 5,836,882 A | 11/1998 | Frazin |
| 5,836,894 A | 11/1998 | Sarvazyan |
| 5,846,202 A | 12/1998 | Ramamurthy et al. |
| 5,851,182 A | 12/1998 | Sahadevan |
| 5,855,554 A | 1/1999 | Schneider et al. |
| 5,865,167 A | 2/1999 | Godik |
| 5,865,743 A | 2/1999 | Godik |
| 5,891,619 A | 4/1999 | Zakim et al. |
| 5,945,674 A | 8/1999 | Dukor |
| 6,002,958 A | 12/1999 | Godik |
| 6,005,916 A | 12/1999 | Johnson et al. |
| 6,014,473 A | 1/2000 | Hossack et al. |
| 6,023,632 A | 2/2000 | Wilk |
| 6,050,943 A | 4/2000 | Slayton et al. |
| 6,056,690 A | 5/2000 | Roberts |
| 6,078,677 A | 6/2000 | Dolleman et al. |
| 6,083,166 A * | 7/2000 | Holdaway ............. B82Y 15/00 606/21 |
| 6,102,857 A | 8/2000 | Kruger |
| 6,109,270 A | 8/2000 | Mah et al. |
| 6,117,080 A | 9/2000 | Schwartz |
| 6,135,960 A | 10/2000 | Holmberg |
| 6,146,897 A | 11/2000 | Cohenford et al. |
| 6,149,441 A | 11/2000 | Pellegrino et al. |
| 6,165,734 A | 12/2000 | Garini et al. |
| 6,190,334 B1 | 2/2001 | Lasky et al. |
| 6,235,038 B1 | 5/2001 | Hunter et al. |
| 6,242,472 B1 | 6/2001 | Sekins et al. |
| 6,245,017 B1 | 6/2001 | Hashimoto et al. |
| 6,256,090 B1 | 7/2001 | Chen et al. |
| 6,289,235 B1 | 9/2001 | Webber et al. |
| 6,292,682 B1 | 9/2001 | Kruger |
| 6,296,489 B1 | 10/2001 | Blass et al. |
| 6,317,617 B1 | 11/2001 | Gilhuijs et al. |
| 6,351,660 B1 | 2/2002 | Burke et al. |
| 6,368,275 B1 | 4/2002 | Sliwa et al. |
| 6,385,474 B1 | 5/2002 | Rather et al. |
| 6,413,219 B1 | 7/2002 | Avila et al. |
| 6,425,869 B1 | 7/2002 | Rafter et al. |
| 6,428,477 B1 | 8/2002 | Mason |

(56) References Cited

U.S. PATENT DOCUMENTS

| | | |
|---|---|---|
| 6,450,960 B1 | 9/2002 | Rather et al. |
| 6,451,013 B1 | 9/2002 | Bays et al. |
| 6,475,150 B2 | 11/2002 | Haddad |
| 6,478,739 B1 | 11/2002 | Hong |
| 6,490,469 B2 | 12/2002 | Candy |
| 6,511,427 B1 | 1/2003 | Sliwa, Jr. et al. |
| 6,527,759 B1 | 3/2003 | Tachibana et al. |
| 6,540,678 B2 | 4/2003 | Rather et al. |
| 6,559,178 B1 | 5/2003 | Zamoyski |
| 6,574,499 B1 | 6/2003 | Dines et al. |
| 6,587,540 B1* | 7/2003 | Johnson ............ G01N 23/2055 |
| | | 378/62 |
| 6,612,988 B2 | 9/2003 | Maor et al. |
| 6,636,584 B2 | 10/2003 | Johnson et al. |
| 6,645,202 B1 | 11/2003 | Pless et al. |
| 6,672,165 B2 | 1/2004 | Rather et al. |
| 6,716,412 B2 | 4/2004 | Unger |
| 6,728,567 B2 | 4/2004 | Rather et al. |
| 6,776,760 B2 | 8/2004 | Marmarelis |
| 6,785,570 B2 | 8/2004 | Nir |
| 6,810,278 B2 | 10/2004 | Webber et al. |
| 6,837,854 B2 | 1/2005 | Moore et al. |
| 6,883,194 B2 | 4/2005 | Corbeil et al. |
| 6,926,672 B2 | 8/2005 | Moore et al. |
| 6,939,301 B2 | 9/2005 | Abdelhak |
| 6,984,210 B2 | 1/2006 | Chambers et al. |
| 7,025,725 B2 | 4/2006 | Dione et al. |
| 7,179,449 B2 | 2/2007 | Lanza et al. |
| 7,285,092 B2 | 10/2007 | Duric et al. |
| 7,346,203 B2 | 3/2008 | Turek et al. |
| 7,497,830 B2 | 3/2009 | Li |
| 7,530,951 B2 | 5/2009 | Fehre et al. |
| 7,556,602 B2 | 7/2009 | Wang et al. |
| 7,570,742 B2 | 8/2009 | Johnson et al. |
| 8,870,771 B2 | 10/2014 | Glide-Hurst et al. |
| 2001/0029334 A1 | 10/2001 | Graumann et al. |
| 2001/0037075 A1 | 11/2001 | Candy |
| 2001/0051774 A1 | 12/2001 | Littrup et al. |
| 2002/0065466 A1 | 5/2002 | Rather et al. |
| 2002/0099290 A1 | 7/2002 | Haddad |
| 2002/0120196 A1 | 8/2002 | Dubberstein et al. |
| 2002/0131551 A1 | 9/2002 | Johnson et al. |
| 2003/0138053 A1 | 7/2003 | Candy et al. |
| 2004/0030227 A1 | 2/2004 | Littrup et al. |
| 2004/0059265 A1 | 3/2004 | Candy et al. |
| 2004/0122325 A1 | 6/2004 | Chambers et al. |
| 2004/0152986 A1 | 8/2004 | Fidel et al. |
| 2004/0167396 A1 | 8/2004 | Chambers et al. |
| 2004/0181154 A1* | 9/2004 | Peterson ............ A61B 8/4472 |
| | | 600/459 |
| 2005/0054924 A1* | 3/2005 | Dione .................... A61B 8/483 |
| | | 600/459 |
| 2005/0165309 A1 | 7/2005 | Varghese et al. |
| 2005/0196025 A1 | 9/2005 | Schofield |
| 2005/0260745 A1 | 11/2005 | Domansky et al. |
| 2006/0009693 A1 | 1/2006 | Hanover et al. |
| 2006/0020205 A1 | 1/2006 | Kamiyama |
| 2006/0064014 A1 | 3/2006 | Falco et al. |
| 2006/0084859 A1 | 4/2006 | Johnson et al. |
| 2006/0085049 A1 | 4/2006 | Cory et al. |
| 2006/0287596 A1 | 12/2006 | Johnson et al. |
| 2006/0293597 A1 | 12/2006 | Johnson et al. |
| 2007/0015949 A1 | 1/2007 | Kaiser |
| 2007/0167823 A1 | 7/2007 | Lee et al. |
| 2007/0282200 A1 | 12/2007 | Johnson et al. |
| 2008/0043036 A1* | 2/2008 | Evertsz ................. G16H 30/20 |
| | | 345/629 |
| 2008/0045864 A1 | 2/2008 | Candy et al. |
| 2008/0058682 A1 | 3/2008 | Azhari et al. |
| 2008/0218743 A1 | 9/2008 | Stetten et al. |
| 2008/0229832 A1 | 9/2008 | Huang et al. |
| 2008/0269812 A1 | 10/2008 | Gerber et al. |
| 2008/0275344 A1 | 11/2008 | Glide-Hurst et al. |
| 2008/0281205 A1 | 11/2008 | Naghavi et al. |
| 2008/0294027 A1 | 11/2008 | Frinking et al. |
| 2008/0294043 A1 | 11/2008 | Johnson et al. |
| 2008/0319318 A1 | 12/2008 | Johnson et al. |
| 2009/0035218 A1 | 2/2009 | Ross et al. |
| 2009/0076379 A1 | 3/2009 | Hamill et al. |
| 2009/0129556 A1 | 5/2009 | Ahn et al. |
| 2009/0143674 A1 | 6/2009 | Nields et al. |
| 2010/0331699 A1 | 12/2010 | Yu et al. |
| 2011/0152685 A1 | 6/2011 | Misono |
| 2013/0267850 A1 | 10/2013 | Berman |
| 2014/0316269 A1 | 10/2014 | Zhang et al. |
| 2015/0005635 A1 | 1/2015 | Glide-Hurst et al. |

FOREIGN PATENT DOCUMENTS

| | | |
|---|---|---|
| EP | 0097917 A1 | 1/1984 |
| EP | 0284055 A2 | 9/1988 |
| EP | 0317049 A2 | 5/1989 |
| EP | 0320444 A1 | 6/1989 |
| EP | 0351610 A2 | 1/1990 |
| EP | 0538241 A2 | 4/1993 |
| EP | 0609922 A2 | 8/1994 |
| EP | 0614651 A1 | 9/1994 |
| EP | 0642762 A2 | 3/1995 |
| EP | 0661029 A1 | 7/1995 |
| EP | 0774276 A2 | 5/1997 |
| EP | 1063920 A1 | 1/2001 |
| GB | 2040642 A | 8/1980 |
| JP | 2005253827 A | 9/2005 |
| JP | 2007181679 A | 7/2007 |
| JP | 2009034521 A | 2/2009 |
| WO | WO-9947046 A1 | 9/1999 |
| WO | WO-0228350 A2 | 4/2002 |
| WO | WO-0230288 A1 | 4/2002 |
| WO | WO-2004061743 A2 | 7/2004 |
| WO | WO-2005057467 A2 | 6/2005 |
| WO | WO-2007023408 A2 | 3/2007 |

OTHER PUBLICATIONS

Hong, A. S., Rosen, E. L., Soo, M. S., & Baker, J. A. (2005). BI-RADS for sonography: positive and negative predictive values of sonographic features. American Journal of Roentgenology, 184(4), 1260-1265. (Year: 2005).*

Yang, J. N., Murphy, A. D., Madsen, E. L., Zagzebski, J. A., Gilchrist, K. W., Frank, G. R., . . . & Gosset, F. R. (1991). A method for in vitro mapping of ultrasonic speed and density in breast tissue. Ultrasonic Imaging, 13(1), 91-109. (Year: 1991).*

Andre et al., "A New Consideration of Diffraction Computed Tomography for Breast Imaging: Studies in Phantoms and Patients," Acoustical Imaging, 21, 379 (1995).

Azhari et al., "Volumetric Imaging with Ultrasonic Spiral CT," Radiol, 212, (1999), 270-275.

Banihashemi, B. et al., "Ultrasound Imaging of Apoptosis in Tumor Response: Novel Preclinical Monitoring of Photodynamic Therapy Effects," Cancer Research, vol. 68, No. 20, Oct. 15, 2008, pp. 8590-8596.

Barlow et al., "Prospective Breast Cancer Risk Prediction Model for Women Undergoing Screening Mammography," J. Nat'l Cancer Institute, 98(17): 1204-1214 (2006).

Boone et al., "Dedicated Breast CT: Radiation Dose and Image Quality Evaluation," Med Phys 221(3): 657-667, (2001).

Boston et al., "Estimation of the Content of Fat and Parenchyma in Breast Tissue Using Mri T1 Histograms and Phantoms," MRI 23: 591-599, (2005).

Boyd, "Quantitative Classification of Mammographic Densities and Breast Cancer Risk: Results from the Canadian National Breast Screening Study," J Nat'l Cancer Institute, 87(9): 670-675, (1995).

Byng et al., The Quantitative Analysis of Mammographic Densities,: Phys Med Biol 39 (1994), 1629-1638.

Cadzow, "Signal enhancement—A composite property mapping algorithm," IEEE Transactions on Acoustics, Speech and Signal Processing, 36(1), (1988), 49-62.

Candy et al., "Signal Processing: The Model-Based Approach," (McGraw Hill. 1986), pp. 178-213.

(56) References Cited

OTHER PUBLICATIONS

Centerline, PortalVision section, Summer 2002 edition, published by Varian Medical Systems.
Chan et al., An Agglomeration Multigrid Method for Unstructured Grids, Contemporary Mathematics, vol. 218, 1998.
Chang et al., "Breast Density Analysis in 3-D Whole Breast Ultrasound Images," IEEE Proc 28th IEEE EMBS Annual International Conference, (2006), 2795-2798.
Chang et al., Kirchhoff migration of ultrasonic images, Materials evaluation, V59, N3, 413-417, 2001.
Chelfouh et al., "Characterization of Urinary Calculi: in Vitro Study of 'Twin king Artifact' revealed by Color-Flow Sonography," AJR Am. J. Roentgenol., 171(4), (1998), 1055-60.
Chen et al., "Projecting Absolute Invasive Breast Cancer Risk in White Women with a Model that Includes Mammographic Density," J. Nat'l Cancer Institute, 98(17), (2006), 1215-1226.
Co-pending U.S. Appl. No. 60/901,903, filed Feb. 16, 2007.
Diederich et al., "The design of ultrasound applicators for interstitial hyperthermia," Ultrasonics Symposium, Proc IEEE 1993 Baltimore, MD, USA, Oct. 31-Nov. 3, 1993, New York, NY, USA, 1215-1219.
Drineas et al., "Distance matrix reconstruction from incomplete distance information for sensor network localization," 3rd Annual IEEE Communications Society on Sensor and Ad Hoc Communications and Networks, Sep. 2006, pp. 536-544.
Duric et al., "Detection of Breast Cancer with Ultrasound Tomography: First Results with the Computed Ultrasound Risk Evaluation (CURE) Prototype," Med Phys, 34(2), (2007).
Dussik, "The Ultrasonic Field as a Medical Tool," Amer J Phys Med, 33(1), (1954), 5-20.
Fjield et al.. "A Parametric Study of the Concentric-Ring Transducer Design for MRI Guided Ultrasound Surgery," J. Acoust. Soc. America, 100 (2), Pt. 1 (1996).
Gervias et al., "Renal Cell Carcinoma: Clinical Experience and Technical Success with Radio-frequency Ablation of 42 Tumors," Radiology, 226, (2003), 417-424.
Glide, "A Novel Approach to Evaluating Breast Density Using Ultrasound Tomography," Dissertation Graduate School of Wayne State University (2007).
Glide et al., "Novel Approach to Evaluating Breast Density Utilizing Ultrasound Tomography," Med Phys, 34(2), (2007), 744-753.
Glide-Hurst, "A New Method for Quantitative Analysis of Mammographic Density," Med Phys, 34(11), (2007), 4491-4498.
Glide-Hurst et al., "A Novel Ultrasonic Method for Measuring Breast Density and Breast Cancer Risk," Med Imaging 2008, Proc SPIE, vol. 6920, 69200Q.
Glide-Hurst et al., "Volumetric breast density evaluation from ultrasound tomography images", Medical Physics, vol. 35, 2008, pp. 3988-3997.
Greenleaf, "Computerized Tomography with Ultrasound," Proc IEEE, 71(3), (1983), 330-337.
Greenleaf, et al. Artificial Cavitation Nuclei Significantly Enhance Acoustically Incuded Cell Transfection. Ultrasound Med & Biol, 24, (1998), 587-595.
Greenleaf et al., "Introduction to Computer Ultrasound Tomography," Computer Aided Tomography and Ultrasonics in Medicine, (1979), North-Holland, 125-136.
Greenleaf et al., "Multidimensional Visualization of Ultrasonic Images," J Acoust Soc Amer, 95 (1994), 2902.
Greenleaf, "Tissue Characterization with Ultrasound: vol. II: Results and Applications," CRC Press, Inc., Boca Raton, Florida, pp. 95-122.
Harmuth, "Sequency Theory: Foundations and Applications, Advances in Electronics and Electron Physics," (Academic Press, 1977) 18-95.
Hayashi, "A New Method of Measuring in Vivo Sound Speed in the Reflection Mode," J Clin Ultrasound, 16(2), (1988), 87-93.
Haykin, "Neural Networks—A Comprehensive Foundation," Prentice Hall, (1994), 236-284.
Hebden et al., "Acoustically Modulated Electrical Impedance Tomography, "Proc SPIE, 1231 (1990), 7-14.
Jellins, "Breast Tissue Characterization," Tissue Characterization with Ultrasound 2 (1986), CRC Press, 95-122.
Jellins et al., "Velocity Compensation in Water-Coupled Breast Echography," Ultrasonics 11(5), (1973), 223-6.
Kaizer et al., "Uitrasonographically Defined Parenchymal Patterns of the Breast: Relationship to Mammographic Patterns and Other Risk Factors for Breast Cancer," Brit J Radiology, 61(722), (1988), 118-24.
Karssemeijer. "Automated Classification of Parenchymal Patterns in Mammograms," Phys Med Biol, 43, (1998), 365-378.
Kerlikowske et al., "Longitudinal Measurement of Clinical Mammographic Breast Density to Improve Estimation Breast Cancer Risk," J. Nat'l Cancer Institute, 99(5), (2007), 386-395.
Klimes, et al., Grid Travel-time Tracing: Second-order Method for the First Arrivals in Smooth Media, PAGEOPH, 1996, 148:539-63.
Knapp et al., "The generalized correlation method for estimation of time delay," IEEE Transactions on Acoustics, Speech and Signal Processing, 24(4), (1976), 320-327.
Kossoff et al., "Average Velocity of Ultrasound in the Human Female Breast," J Acoust Soc America, 53(6), (1973), 1730-6.
Li et al., Breast Imaging Using Transmission Ultrasound: Reconstructing Tissue Parameters of Sound Speed and Attenuation, 2008 International Conference on BioMedical Engineering and Informatics, IEEE Computer Society, 708-712.
Li et al., Comparison of Ultrasound Attenuation Tomography Methods for Breast Imaging, Medical Imaging 2008: Ultrasonic Imaging and Signal Processing, Proc. of SPIE., vol. 6920, 692015-(1-9), 2008.
Li et al., "In Vivo Breast Sound-Speed Imaging with Ultrasound Tomography", Ultrasound in Med & Bioi., vol. 35, No. 10, 2009, pp. 1615-1628.
Li et al., Refraction Corrected Transmission Ultrasound Computed Tomography for Application in Breast Imaging, Med. Phys. 37(5), May 2010, 2233-2246.
Li et al., "Clinical Breast Imaging Using Sound-Speed Reconstructions of Ultrasound Tomography Data," Med Imaging 2008, Proc SPIE, vol. 6920, 6920009.
Louvar et al., "Correlation of Color Doppler Flow in the Prostate with Tissue Microvascularity," Cancer 1 :83(1), (1998), 135-40.
Marias, "Automatic Labelling and BI-RADS Characterisation of Mammogram Densities," Proc 2005 IEEE, Sep. 1-4, 2005, pp. 6394-6398.
Mast, "Empirical Relationships Between Acoustic Parameters in Human Soft Tissues," Acoust Research Letters Online, Nov. 16, 2000, pp. 37-42.
Masugata et al., "Relationship Between Myocardial Tissue Density Measured by Microgravimetry and Sound Speed Measured by Acoustic Microscopy," Ultrasound in Med & Biol, 25(9), (1999), 1459-1463.
McCormick et al., Multigrid Solution of a Linearized, regularized least-squares problem in electrical impedance tomography, Inverse Problems 9, 1993, 697-713.
Metz, "Basic Principles of ROC Analysis"; Semin Nucl Med., Oct. 8, 1978 (4):283-98.
Metz, "Receiver Operating Characteristic Analysis: A Tool for the Quantitative Evaluation of Observer Performance and Imaging Systems," J Am Coli Radiol 2006; 3: 413-422.
Metz, "ROC Methodology in Radiologic Imaging"; Invest Radiol., Sep. 21 1986, (9):720-33.
Miller et al., "Sonoporation of Cultured Cells in the Rotating Tube Exposure System," Ultrasound Med & Biol, 25 (1999), 143-149.
Mitchell, An Introduction to Genetic Algorithms, pp. 8-11. 35-78. 155-179 (MIT Press, 1996).
Nelson et al., "Interactive Acquisition, Analysis and Visualization of Sonographic Volume Data," International J Imaging Sys and Tech, 8(26), (1997), 26-37.
Noble et al., "Spleen Hemostasis Using High-Intensity Ultrasound: Survival and Healing," J. Trauma Injury, Infection, and Critical Care, 53(6), (2002), 1115-1120.
Notice of allowance dated Jun. 20, 2014 for U.S. Appl. No. 12/115,174.

(56) References Cited

OTHER PUBLICATIONS

Office action dated Jun. 6, 2011 for U.S. Appl. No. 12/115,174.
Office action dated Oct. 7, 2013 for U.S. Appl. No. 12/115,174.
Office action dated Nov. 25, 2011 for U.S. Appl. No. 12/115,174.
Oh et al., Multigrid Tomographic Inversion with Variable Resolution Data and Image Spaces, IEEE Transactions on Image Proessing, vol. 15, No. 9, Sep. 2006.
Ophir et al., "Elastography: Ultrasonic Estimation and Imaging of the Elastic Properties of Tissues," Proc Instn Mech Engrs, 213(Part H), (1999), 203-233.
Palomares et al., "Mammographic Density Correlation with Gail Model Breast Cancer Risk Estimates and Component Risk Factors," Cancer Epidemiol Biomarkers Prev, 15(7), (2006), 1324-1330.
Quan et al., Sound-speed Tomography using First-arrival Transmission Ultrasound for a Ring Array, Medical Imaging 2007: Ultrasonic Imaging and Signal Processing, Proc. of SPIE, vol. 6513.
Robinson et al., "Quantitative Sonography," Ultrasound in Med & Biol, 12(7): 555-65, (1986).
Schmidt et al., "Modification of Kirchhoff Migration with Variable Sound Speed and Attenuation for Tomographic Imaging of the Breast," Proc. of SPIE, vol. 7968, Mar. 25, 2011.
Sehgal et al., "Visualization of Breast Calcification by Acoustic Resonance Imaging," Radiology Supplement, 84th Scientific Assembly and Annual Meeting, Nov. 29-Dec. 4, 1998 presented in McCormick Place, Chicago, Illinois, vol. 209, listing: 1150 (1998).
Shi et al., "Effects of Pressure Changes on Harmonic and Subharmonic Response of US Contrast Microbubbles," 84th Scientific Assembly and Annual Meeting, Nov. 29-Dec. 4, 1998, presented in McCormick Place, Chicago, Illinois, vol. 209, listing: 1154 (1998).
Singh, Seema et al., "Color Doppler Ultrasound as an Objective Assessment Tool for Chemotherapeutic in Response Advanced Breast Cancer," Breast Cancer, 2005, vol. 12, No. 1, 2005, pp. 45-51.
Teubner et al., "Comparative Studies of Various Echomammography," Ultraschall in Der Medizin, 3(3) (1982), 109-18, Thieme Verlag, Stuttgart/New York.
U.S. Appl. No. 14/486,551 Office Action dated Mar. 9, 2018.
Vaezy et al., "Real-Time Visualization of High-Intensity Focused Ultrasound Treatment Using Ultrasound Imaging," Ultrasound in Med & Biol, 27(1), (2001), 33-42.
Walach et al., Local Tissue Attenuation Images Based on Pulsed-Echo Ultrasound Scans, IEEE Transactions on Biomedical Engineering, vol. 36. No. 2, Feb. 1989.
Wei et al., "Correlation Between Mammographic Density and Volumetric Fibroglandular Tissue Estimated on Breast MR Images," Med Phys, 31(4), (2004), 933-942.
Weiwad et al., "Direct Measurement of Sound Velocity in Various Specimens of Breast Tissue," Invest Radiol, 35(12), (2000), 721-6.
Wiskin et al., "Full Inverse Scattering vs. Born-like Approximation for Imaging in a Stratified Ocean," Proc. Eng. in Harmony with the Ocean, (Oceans '93), Victoria, British Columbia (Oct. 1993).
Wolfe, "Risk for Breast Cancer Development Determined by Mammographic Parenchymal Pattern," Cancer, 37(5), (1976), 2486-2493.
Xu, et al., "A Study of 3-Way Image Fusion for Characterizing Acoustic Properties of Breast Tissue," Medical Imaging 2008: Ultrasonic Imaging and Signal Processing, Feb. 16, 2008.
Yaffe, "Breast Cancer Risk and Measured Mammographic Density," Eur J Cancer Prevention, 7(1), (1998), S47-55.
Yaman, C. et al., "Three-Dimensional Ultrasound to Assess the Response to Treatment in Gynecological Malignancies," Gynecologic Oncology, Academic Press, vol. 97, No. 2, May 1, 2005, pp. 665-668.
Yankelevitz et al., "Small Pulmonary Nodules: Volumetrically Determined Growth Rates Based on CT Evaluation," Radiology, 217, (2000), 251-256.
Zhang et al., A Comparison of Material Classification Techniques for Ultrasound Inverse Imaging, J. Acoust. Soc. Am., 111 (1), Pt. 1, Jan. 2002.

* cited by examiner

Fatty     Scattered     Heterogeneous     Dense

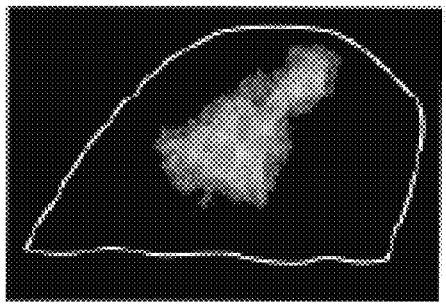
FIG. 8A
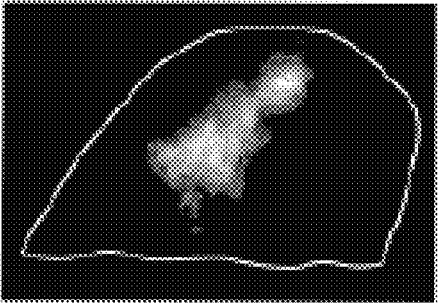
FIG. 8B
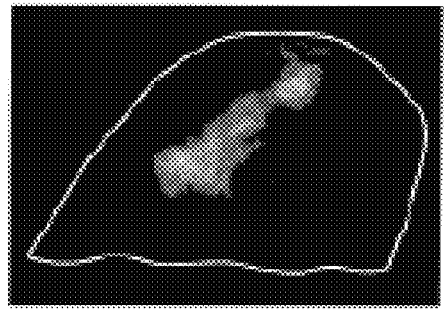
FIG. 8C
FIG. 8D
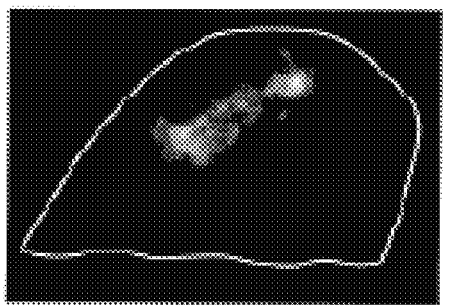
FIG. 8E
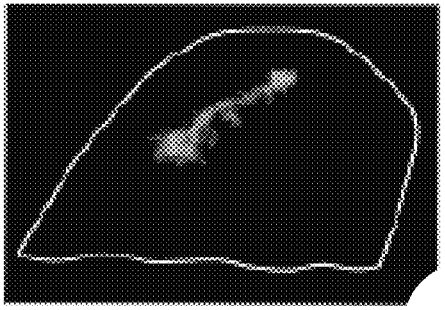
FIG. 8F
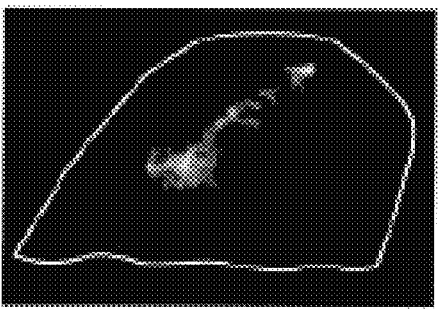
FIG. 8G
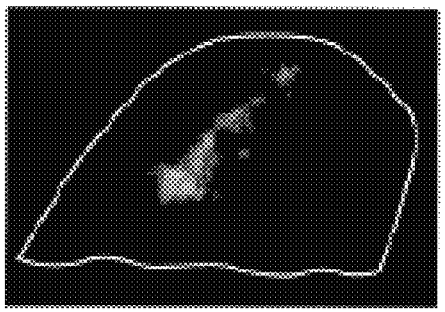
FIG. 8H

PATIENT INTERFACE SYSTEM

CROSS-REFERENCE TO RELATED APPLICATIONS

This application is continuation application of U.S. application Ser. No. 14/486,551 filed 15 Sep. 2014, which is a continuation-in-part application of U.S. application Ser. No. 12/115,174 filed 5 May 2008, now U.S. Pat. No. 8,870,771, which claims the benefit of U.S. Provisional Application Ser. No. 60/915,946 filed 4 May 2007, which are each incorporated in their entirety herein by this reference.

STATEMENT AS TO FEDERALLY SPONSORED RESEARCH

This invention was made with Government support under Grant R44CA165320 awarded by the National Institutes of Health (NIH) through the National Cancer Institute. The Government has certain rights in the invention.

TECHNICAL FIELD

This disclosure relates to medical devices and more particularly relates to a method and apparatus for determining breast density and assessing cancer risk utilizing acoustic parameters.

BACKGROUND

According to the World Health Organization, breast cancer is the second most common type of cancer and the fifth most common cause of cancer death. In view of the commonality of breast cancer, diligent individuals subject themselves to regular mammograms for the purpose of detecting an existence of breast cancer.

An ancillary benefit of having a mammogram conducted is the ability of the radiologist to determine a radiographical density of the participant's breast tissue due to the fact that there is a prognostic relationship between breast density and cancer risk. In general, it is known in the art that the radiographical density of a breast illustrated within a mammogram may vary due to differences in the amount of fat, connective tissues, and epithelial tissues that are present. For example, because fibroglandular and connective tissues (i.e. glands, ducts, and fibers) have a relatively high x-ray attenuation, fibroglandular and connective tissues may appear to be radiographically dense/light on radiographic films. By contrast, fat has a relatively low x-ray attenuation and therefore appears to be the least radiographically dense/dark, when compared to the remaining breast tissue. Because of the distinct differences in x-ray attenuation between fat and fibroglandular tissue, segmentation of fibroglandular tissue from the rest of the breast is possible.

A known breast density estimation standard may be based upon a four-category Breast Imaging Reporting and Data Systems (BI-RADS) lexicon. Upon visually assessing a mammogram, a radiologist may classify the radiographical image of the breast into one of four BI-RADS compositional categories defined as: 1: Fatty, 2: Scattered, 3: Heterogeneous, and 4: Dense. Women whose breasts are categorized in the BI-RADS 4/densest breast category are four-to-six times more likely to develop breast cancer than those categorized as BI-RADS 1/fatty Because the above standard in breast density estimation involves a radiologist's visual assessment of a mammogram, this assessment is subjective and relies on the perception of the radiologist. While such a subjective density classification is quick to use and widely employed, it has been proven to be limited due to considerable intra- and inter-reader variability of a radiologist.

Further, as also known in the art, the use of mammography is not ideal because of the associated radiation exposure to the participant that is undergoing breast evaluation Even further, a mammogram is a two-dimensional projection which, by definition, does not provide an accurate, three-dimensional volumetric estimation of the breast density due to the tissue thickness not being taken into account. Even further, it is also known that women are apprehensive about mammography due to the uncomfortable compression of the breast associated with the scan.

Accordingly, there is a need in the art for an improved method and apparatus for determining breast density. In an embodiment, the novel method and apparatus is a non-ionizing method and apparatus. In an embodiment, the determined breast density may be utilized for assessing cancer risk.

Further, because the novel methodology yields parameters that are associated with high breast density, which, in turn, may be associated with increased breast cancer risk, it will be appreciated that data arising from the novel methodology may be utilized to assess cancer risk directly without the intermediate step of determining breast density.

Yet even further, by identifying women having high breast density, further preventative measures can be implemented.

BRIEF DESCRIPTION OF THE FIGURES

FIGS. 8A-8H each illustrates a graphical representation of a lesion associated with breast tissue over time based upon acoustic parameters.

DESCRIPTION OF THE PREFERRED EMBODIMENTS

The Figures illustrate an exemplary embodiment of a method and apparatus for determining breast density and assessing cancer risk utilizing acoustic parameters in accordance with an embodiment of the invention. Based on the foregoing, it is to be generally understood that the nomenclature used herein is simply for convenience and the terms used to describe the invention should be given the broadest meaning by one of ordinary skill in the art. Further, although an embodiment of the invention described in the foregoing disclosure is related to the analysis of breast tissue, it will be appreciated that the invention is not meant to be limited to breast tissue; for example, it will be appreciated that the invention may be utilized to analyze organ tissue, such as, for example, a liver. As such, the foregoing methodologies disclosed in the foregoing disclosure may be utilized to assess the risk of, for example, cancer of the liver.

1. Apparatus

Figure 1:
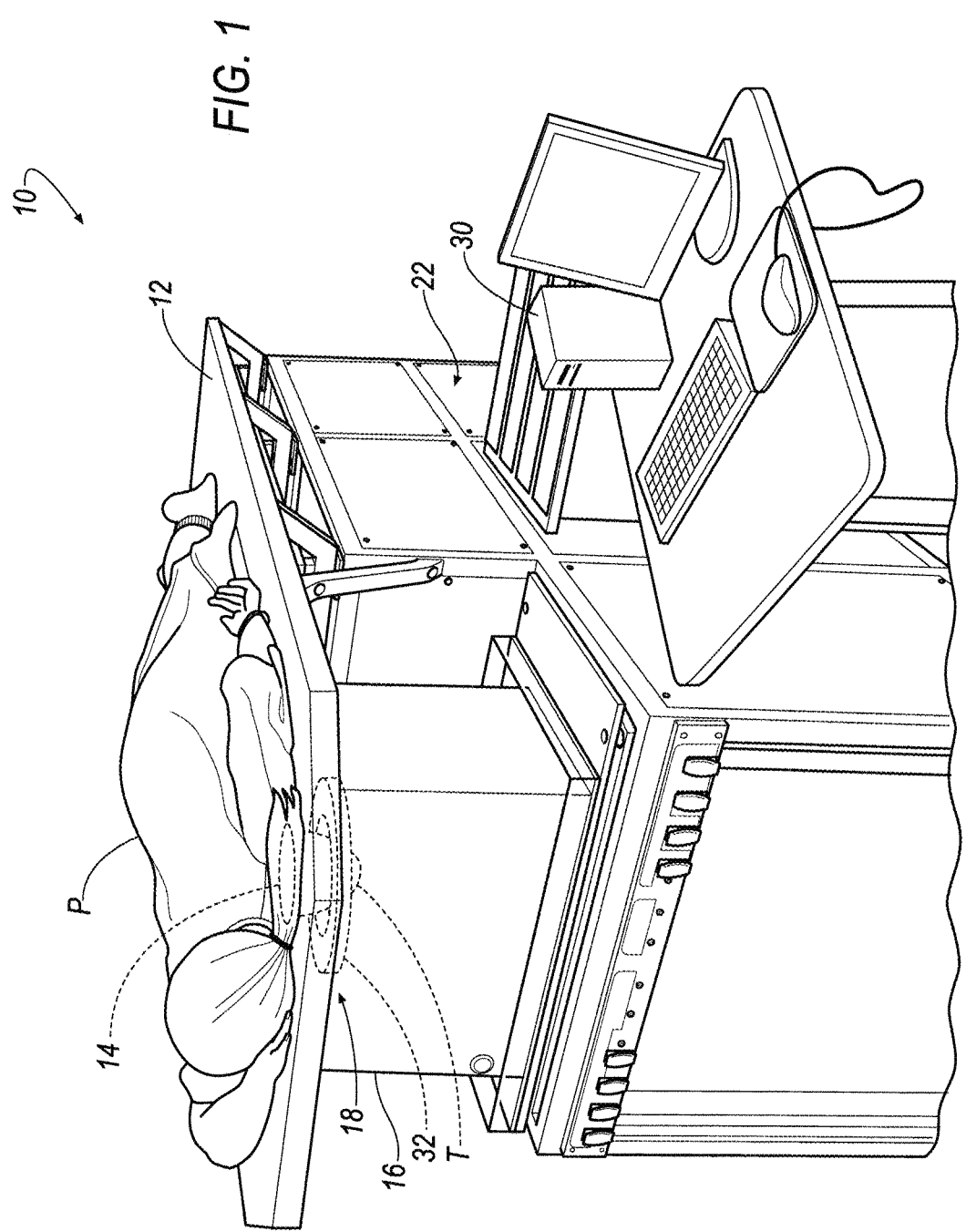
FIG. 1 is an environmental view of a non-ionizing, non-compressing, volumetric ultrasound tomography apparatus in accordance with an exemplary embodiment of the invention.

Referring to FIG. 1, an environmental view of a non-ionizing, non-compressing, volumetric ultrasound tomography apparatus 10 is shown according to an embodiment. According to an embodiment, the apparatus 10 includes a platform 12 having an opening 14 and a tank 16 having an imaging device 18 disposed in the tank 16.

Because the apparatus 10 utilizes ultrasound to analyze the tissue, T, there is no ionizing radiation exposure to the patient, P. In addition, because the tissue is immersed in a fluid within the tank 16, there is no compression of the tissue, T, which may otherwise cause discomfort to the patient, P. Even further, it will be appreciated that the apparatus 10 provides a volumetric, three-dimensional analysis of the tissue, T, as opposed to a less accurate, two-dimensional analysis of the tissue, T. Finally, it will be appreciated that the time it takes for apparatus 10 to scan a breast tissue volume is typically less than 90 seconds.

In an embodiment, the patient, P, is a female, and the tissue, T, being analyzed is breast tissue. However, it will be appreciated that the patient, P, being examined is not limited to being a female, and, the tissue, T, being scrutinized is not limited to breast tissue.

In operation and as shown in FIG. 1, the patient, P, is situated in a face-down position on the platform 12 such that the breast tissue, T, is inserted through the opening 14 and into the tank 16. As illustrated, the opening 14 is substantially aligned with the location of the tank 16, which is located under the platform 12, relative the patient, P. Once inserted through the opening 14, the breast tissue, T, is immersed in fluid within the tank 16.

Figure 2:
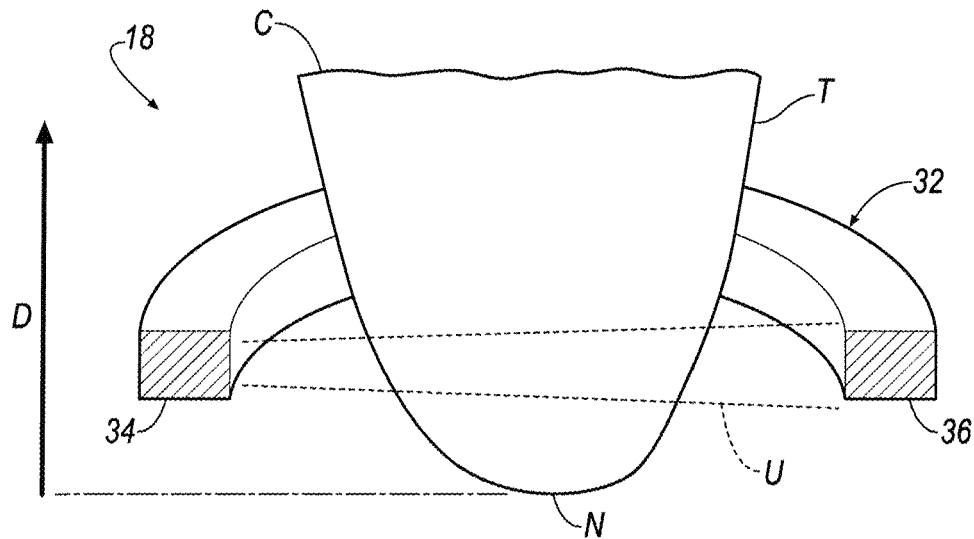
FIG. 2 is a perspective, cross-sectional view of an ultrasound transducer ring of the ultrasound tomography apparatus of FIG. 1 relative a breast in accordance with an exemplary embodiment of the invention.

Referring to FIG. 2, the imaging device 18 is shown according to an embodiment. The imaging device 18 may be an ultrasound tomography device comprising a transducer ring 32. As shown in FIG. 1, the transducer ring 32 of the imaging device 18 is immersed in the fluid. As is shown, the transducer ring 32 includes a transmitter end 34 and a receiver end 36.

According to an embodiment, the transmitter end 34 and receiver end 36 may be constructed from any desirable material, such as, for example, an array of piezoelectric elements, an array of ceramic elements, an array of electromechanical elements, an array of magnetostrictive elements, or the like. Even further, in an embodiment, it will be appreciated that the array may be static, a stationary pair, a rotated pair, or the like. In an embodiment, the array may comprise a two-dimensional array, or, alternatively, a three-dimensional array that may be translated along different planes to enable three-dimensional data collecting, which is described in greater detail below.

In an embodiment, an ultrasound caliper device including a transmitting end and receiving end, can also be used in a substantially similar manner as the transducer ring 32 in order to collect data. If an ultrasound caliper is utilized, acoustic parameters can be obtained and evaluated without the construction of a graphical image. Further, the use of an ultrasound caliper provides a simple, hand-held device and therefore eliminates the use of a relatively larger tank 16 including, for example, a water bath.

Referring to FIGS. 1 and 2, once the breast tissue, T, is inserted into the tank 16, the breast tissue, T, is circumscribed by the transducer ring 32. Thus, ultrasound analysis of the breast tissue, T, may be conducted by transmitting sound waves, U, from the transmitter end 34 to the receiver end 36 by way of the fluid and breast tissue, T, disposed within the tank 16.

To obtain a volumetric, three-dimensional analysis of the breast tissue, T, the transducer ring 32 is initialized to a start position within the tank 16. Once initialized to the desired starting position, the sound-waves, U, are emitted as the transducer ring 32 moves in a direction according to the arrow, D, toward the platform 12/chest, C, of the patient, P, to an end position. The fluid, which may be, for example, water, is known to have well-defined sound speed parameters that serve as both a coupling medium and a matching layer between the breast tissue, T, and the transducer elements 34, 36.

Although the above-disclosed embodiment is described to include an apparatus 10 having a tank 16 holding a fluid, it will be appreciated that the invention is not limited to the use of the apparatus 10 for obtaining tissue data of a breast. For example, coupling fluids other than water, such as, for example, acoustic gels, may be applied to an outer surface of the breast; and, in an embodiment, a transducer may directly contact the breast by way of the acoustic gel. In another embodiment, a single transducer in conjunction with acoustic mirrors may also be utilized instead of the apparatus 10. A further alternative embodiment may include measurements in the time domain such that collected data from one or more transducers is not related to imaging data associated with the apparatus 10.

2. Determining Breast Density

In an embodiment, the sound waves, U, may be utilized to determine whole-breast acoustic measures. In an embodiment, the sounds waves, U, are utilized to determine an average whole breast acoustic sound speed velocity. The average whole breast acoustic sound speed velocity may then be utilized as an indicator of the density of the breast tissue, T.

In an embodiment, the speed of the sound waves, U, is based on signals transmitted through the breast tissue, T, and are used to generate graphical maps of the sound speed distribution. In an embodiment, the sound speed may be provided in a scale of, for example, meters-per-second (m/s). In another embodiment, graphical maps of sound speed distribution are not created such that a sound speed measurement, calculation or the like representing an entire breast may be provided. In an embodiment, the sound speed measurement, calculation or the like may be utilized as a factor for assessing cancer risk.

Figure 3:
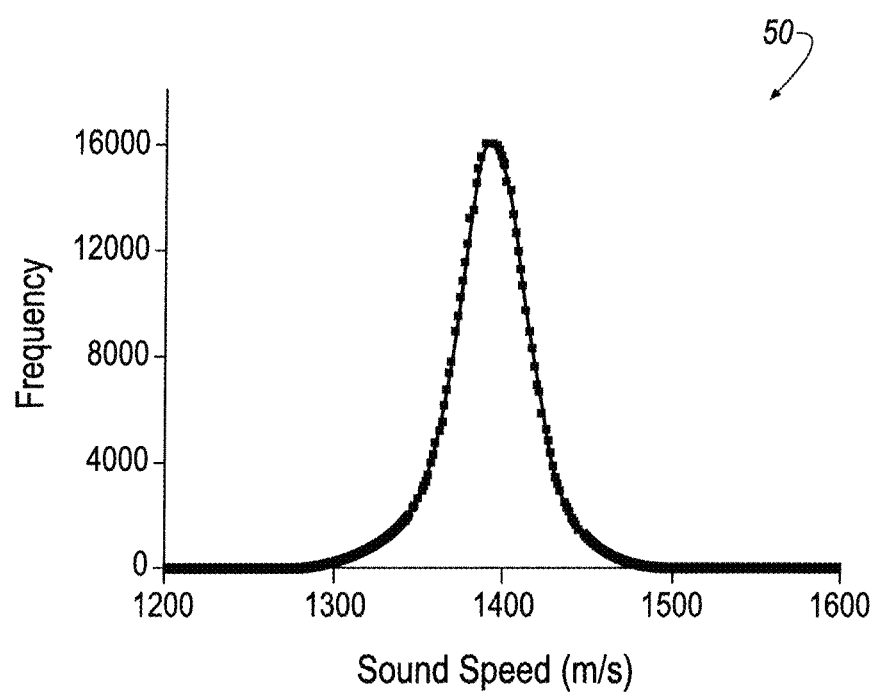
FIG. 3 is a tissue sound speed frequency histogram of a subject obtained from the apparatus of FIG. 1.

In an embodiment, whole breast acoustic velocity may be defined as a global sound speed measure obtained from a sound speed histogram 50 (see, e.g., FIG. 3), which is developed from tomograms that are produced, in an embodiment, by the apparatus 10. Referring to Equation 1 below, under the assumption that the tissue, T, is fluid-like, the speed of sound (V) has the following relationship to an elastic constant (c) and material density (p) of the material through which the sound waves, U, travel:

$$V = \mathrm{sqrt}(c/p) \qquad (1)$$

From this relationship, the average velocity 52 (see, e.g. FIG. 4) through tissue, T, would be related to the breast density and elasticity. Water, which has similar properties to tissue, T, has a bulk elastic constant of $2.2 \times 10^9$ N/m$^2$. In vitro and in vivo data both support the relationship of increased sound speed with increased density of material.

To provide the histograms 50, image stacks are created for each segment of the patient's breast as the transducer ring 32 moved from its initialized start position to its end position. Because an image stack corresponds to the entire breast volume, the histograms 50 represent the statistical distribution of all sound speed voxels within that particular breast. From the histogram 50, an overall mean sound speed value for each breast is obtained to provide a single-value estimate of the volumetric average of the sound speed velocity 52 of the whole breast.

It will be appreciated, however, that measurements of an overall mean is not intended to limit the present invention and that other measures may be utilized. For example, other measures may include, but are not limited to a median, mode, midrange, skewness, kurtosis, or the like.

It will be appreciated that an overall sound speed is not meant to limit the present invention and that other measures of acoustical data may be utilized. For example, other acoustical data may include, but are not limited to attenuation, reflection, elasticity, or the like. Also, derivations of acoustical properties other than measures of central tendency may be used to derive a whole breast density measure. Examples could include parameters such as texture (2D or 3D, skewness, kurtosis, etc.) and pattern (fractal dimension, lacunarity, etc.). Even further, data integration could also be used for whole breast density acoustical measures, such as combining features from several temporal scans, different acoustical parameters, etc.

Figure 4:
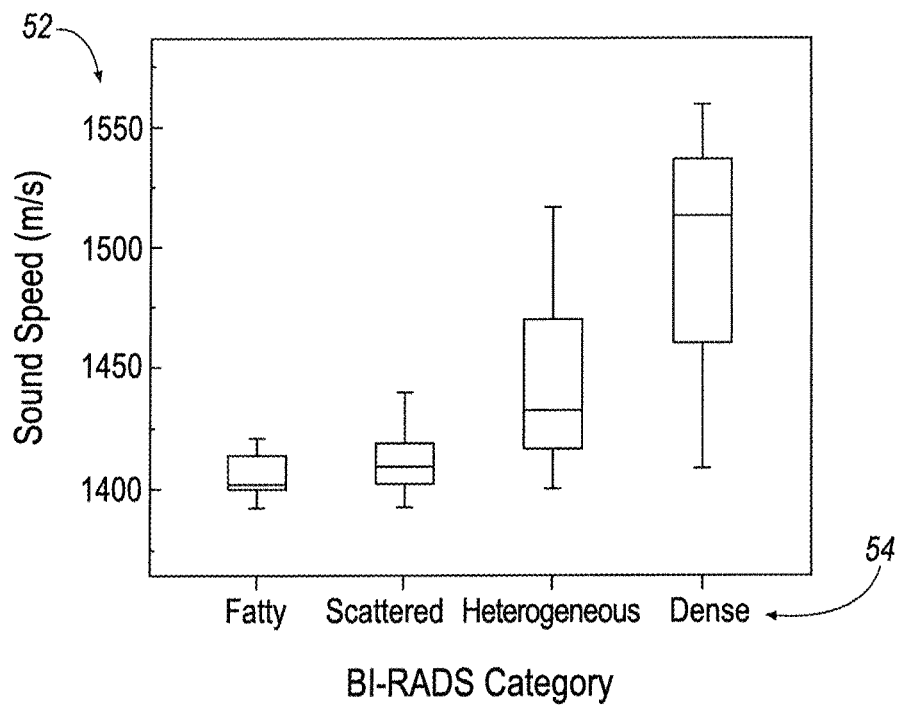
FIG. 4 is a plot of mean tissue sound speed for a group of subjects according to a BI-RADS compositional categorization.

Referring to FIG. 4, as a basis to correlate breast density and the average acoustic sound speed velocity 52, a sampling of average sound speed histograms 50 were arranged against corresponding qualitative BI-RADS breast density measures 54 for each subject of the sampled population. As is known in the art, BI-RADS compositional categories are a known breast density estimation standard (i.e., classification in BI-RADS: 1-3 means there is a lesser cancer risk than a classification of BI-RADS:4). The use of BI-RADS in FIG. 4 is for comparative purposes to illustrate the inventive concept of utilizing non-ionizing acoustics to quantify a cancer risk assessment of a biological tissue such as, for example, breast tissue, T.

Accordingly, to establish the data shown in FIG. 4, each patient, P, in the sampled population were subjected to an acoustic signal such that whole-breast sound speed data could be measured and analyzed for obtaining an acoustic measure of each patient's breast tissue, T. Prior to or after obtaining the acoustic measure, a BI-RADS classification for each patient was also established. Accordingly, as illustrated in FIG. 4, data for the entire sampled population was compiled. It can be seen that as the average acoustic sound speed velocity 52 of each patient's breast tissue, T, increases, there is also an increase, in a corresponding fashion, with a radiologist's qualitative assessment of the BI-RADS density of each subject patient, P.

In an embodiment, the relationships of the data shown in FIG. 4 are expressed as follows. According to an embodiment, average volumetric sound speed velocities 52 ranging between approximately 1400-1415 m/s relate to a fatty (BI-RADS: 1) categorization. According to an embodiment, average volumetric sound speed velocities 52 ranging between approximately 1405-1420 m/s relate to a scattered (BI-RADS: 2) categorization. According to an embodiment, average volumetric sound speed velocities 52 ranging between approximately 1420-1465 m/s relate to a heterogeneous (BI-RADS: 3) categorization. According to an embodiment, average volumetric sound speed velocities 52 ranging between approximately 1460-1575 m/s relate to a dense (BI-RADS: 4) categorization.

According to an alternative embodiment, average volumetric sound speed velocities 52 ranging between approximately 1438-1450 m/s relate to a fatty (BI-RADS: 1) categorization. According to an embodiment, average volumetric sound speed velocities 52 ranging between approximately 1450-1463 m/s relate to a scattered (BI-RADS: 2) categorization. According to an embodiment, average volumetric sound speed velocities 52 ranging between approximately 1463-1476 m/s relate to a heterogeneous (BI-RADS: 3) categorization. According to an embodiment, average volumetric sound speed velocities 52 greater than 1476 m/s (e.g., ranging between approximately 1476-1489 m/s) relate to a dense (BI-RADS: 4) categorization.

It will be appreciated that by using the above-described data associated with FIG. 4 or data according to the alternative embodiment as a frame of reference, sound speed threshold values can be determined and utilized alone (without determining density of breast tissue, T) to identify women who are at increased breast cancer risk. To serve as an example, if a patient's breast tissue, T, is defined to have a sound speed measure of, for example, 1402 m/s (or 1442 m/s), the measure falls into the range of 1400-1415 m/s (or 1438-1450 m/s), and, as such, the patient, P, may be said to have a lesser risk of developing breast cancer in the future due to the fact that the 1402 m/s (or 1442 m/s) measure falls in the range of 1400-1415 m/s (or 1438-1450 m/s), which is associated with a fatty/BI-RADS: 1 categorization.

Thus, the four sound speed ranges described above may establish, in an embodiment, the basis of a cancer risk model such that a sound speed measure falling into the range of 1460-1575 m/s (or 1476-1489 m/s) may be said to have a greatest risk of developing breast cancer than sound speed measures other ranges. Accordingly, by obtaining a measure (e.g., sound speed) and comparing the measured value against the above ranges, a quantified risk assessment may be obtained.

It can be appreciated that the basis of a breast cancer risk evaluation model using acoustic parameters is not limited to comparisons with BI-RADS compositional categories, and instead, more quantitative evaluation methods can be considered (i.e. computer-assisted segmentation of mammograms using interactive thresholding or automated segmentation). Further, it can be appreciated that a breast cancer risk evaluation model can be developed independent of any association with other breast density evaluation techniques.

It will be appreciated, however, that although sound speed is described above, a measured distribution of an acoustic signal is not limited to sound speed; for example, the measured distribution of acoustic signals may also be applied to attenuation, reflectivity, elasticity and the like. Further, the cancer risk model may be further refined by also applying additional data to, for example, the measured sound speed. In an embodiment, the additional data may include, for example, one or more of age, menopausal status, age at menarche, parity, age at first birth, number of first and second degree relatives with breast cancer, prior breast biopsies, hormonal usage, history of atypical hyperplasia, or history of lobular carcinoma in situ, and the like.

3. Determining Breast Density Using a Tissue Volume Separator

Figure 5:
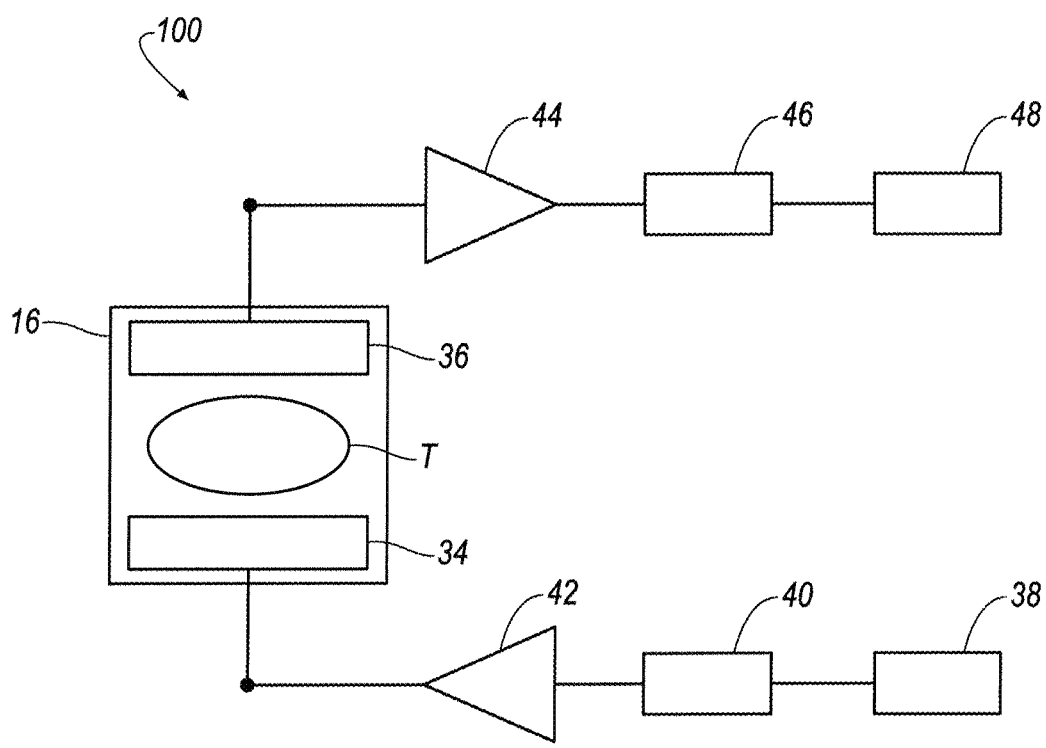
FIG. 5 is a block diagram of an apparatus for determining ultrasound percent density in accordance with an exemplary embodiment of the invention.

Referring now to FIG. 5, a block diagram 100 for a tissue volume separator from acoustic data provided by the apparatus 10 is shown generally at 100 according to an embodiment. The block diagram generally includes a waveform generator 38, a digital-to-analog converter 40, an acoustic transmit amplifier 42, the transmitter end 34, the receiver end 36, an acoustic receive amplifier 44, an analog-to-digital converter 46, and tissue volume separator value generator 48.

Functionally, the waveform generator 38 creates a series of digital signals. The digital signals are sequentially sent to the digital-to-analog converter 40 that converts each signal to a corresponding analog out-put signal which is then amplified by the transmit amplifier 42. The amplified signal drives the transmitter end 34, which converts the electrical analog signal into an acoustical signal, which propagates through the fluid in the tank 16 to the receiver end 36. The receiver end 36 converts the acoustical signal back into an electrical analog received signal, which may be amplified by a receive amplifier 44. The received signal may be digitized by the analog-to-digital converter 46.

The sampling rate of the analog-to-digital converter 46 can be set to digitize the analog signal at the Nyquist (or other) rate corresponding to the frequency used to drive the transducers 34, 36. The resulting digital data stream may be stored in the tissue volume separator 48, which may include a digital storage system in the form a random access memory, a hard drive, or the like. It will be appreciated that the tissue volume separator may be a stand-alone device, or, alternatively, be incorporated in the electronics 22, or, alternatively be incorporated in the central processing unit 30.

To determine the tissue volume separator results of the breast tissue, T, the processor of the breast density factor 48 is concerned with breast sound speed. According to an embodiment as seen in Equation 2 below, a tissue density factor, TDF, can be defined by:

$$\text{TDF} = (\text{High Sound Speed Volume})/(\text{Total Breast Volume}) \quad (2)$$

The denominator (i.e., Total Breast Volume) is further defined as the total (summed) integrated areas of breast sound speed tomograms. The numerator (i.e., High Sound Speed Volume Data) is further defined as the integrated area of sound speed regions from the sound speed tomograms that are considered to be of high sound speed value. The can be determined by the areas exceeding a sound speed threshold value. This threshold for determining high sound speed is not meant to limit the present invention and that other techniques used to segment higher sound speed regions may be utilized. For example, other techniques may include, but are not limited to semi-automated or automated: k-means or fuzzy clustering, segmentation in the frequency domain or time domain, artificial neural networks, or the like. Further, the TDF can be determined from data arising directly from a three-dimensional (3D) volume as opposed to a stack of two dimensional (2D) tomograms.

It can be appreciated that using this methodology, sound speed threshold values can be determined and applied to an entire population, thereby associating TDF value of a subject to identify the likelihood of breast cancer risk. Similarly, tissues other than fatty and fibroglandular may be further segmented by volumetric assessment of other ultrasound parameters. In an embodiment, it will be appreciated that the TDF is not restricted to a ratio, but also, an absolute integrated area of dense tissue and total breast tissue as indicators of breast cancer risk.

Figure 6A:
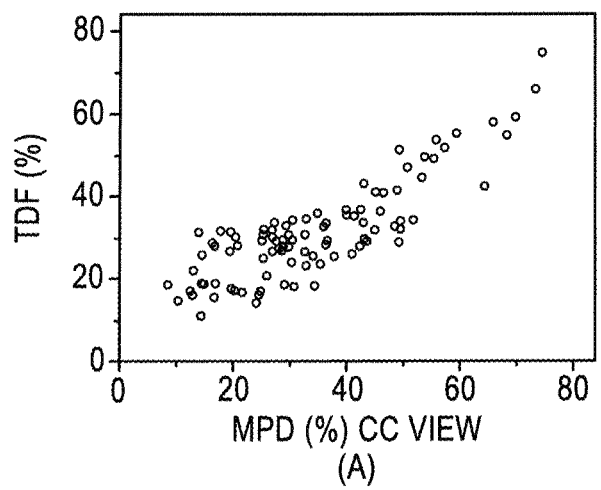
FIG. 6A is a plot of tissue density factor (TDF) according to quantitatively obtained mammographic percent density.
Figure 6B:
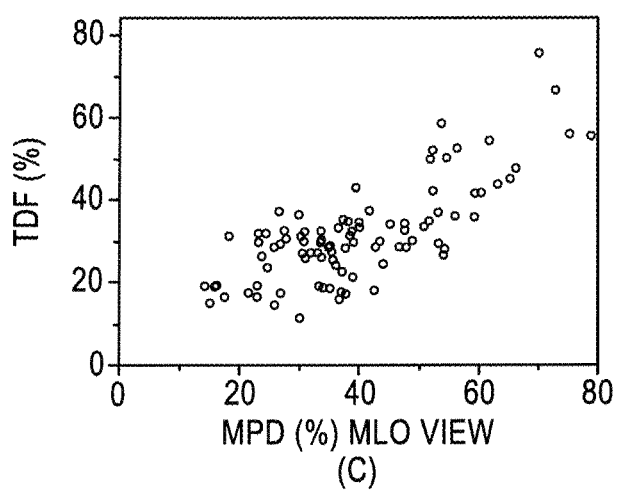
FIG. 6B is a plot of tissue density factor (TDF) according to quantitatively obtained mammographic percent density.

Referring to FIGS. 6A and 6B, as a basis to correlate TDF and breast density, the TDF is shown along the y-axis and quantitative mammographic percent density using semi-automated segmentation routines is shown along the x-axis. The TDF was calculated according to Equation 2 above for a plurality of patients and the results are correlated to a corresponding quantitative mammographic percent density (MPD) measures for each patient of the plurality of patients. For illustrative purposes, FIG. 6A provides an MPD for the craniocaudal (CC) view and FIG. 6B provides an MPD for the mediolateral oblique (MLO) (MLO) view. In general, FIGS. 6A and 6B provides evidence that as TDF of the breast tissue, T, increases, the MPD increases in a corresponding fashion.

It will be appreciated that, similar to providing several different volumetric distributions of imaging data, the associated tissue characterizations and assorted tissue types can be displayed in multiple different distributions. While sound speed has been currently used to separate fatty from parenchymal breast tissues for volumetric density estimates, other imaging data (such as attenuation, reflectivity, elasticity, etc.) may allow further volumetric separation of cystic areas, and benign and malignant tumors from the current separation of fatty and parenchymal tissue by sound speed alone.

4. Applications of Acoustic and TDF Measurements of the Breast

Multiple measurements of the breast can be conducted in space in a repeated fashion by positioning the transducer ring 32 and discretely measuring the breast tissue, T, in two-dimensional cycles until full, three-dimensional coverage of the breast tissue, T, is achieved. As such, discrete, two-dimensional measurements of the breast tissue, T, may be obtained to provide coverage of the breast tissue, T, at different cross-sections to simulate a three-dimensional analysis of the breast tissue, T, by 'stacking' a plurality of discrete, two-dimensional measurements. Although it is possible to 'stack' a plurality of discrete, two-dimensional measurements to provide a three-dimensional measurement, it will be appreciated that a direct three-dimensional measurement with a two-dimensional array is also possible.

Figures 7A, 7B, 7C, 7D:
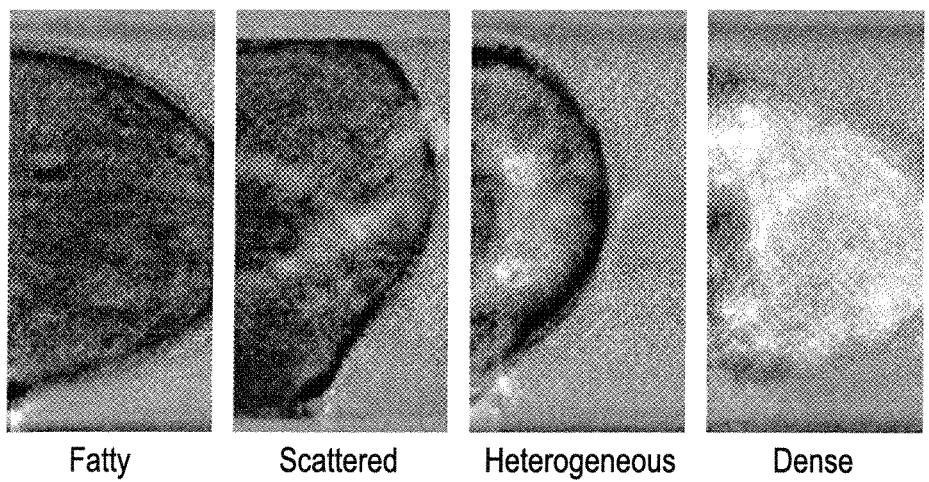
FIGS. 7A-7D each depict a graphical representation of intensity projections of three-dimensional sound speed data for a typical breast from each BI-RADS compositional category (1: fatty to 4: dense), wherein the white regions demonstrate high sound speed values relative to the darker lower sound speed regions.

It will be appreciated that having three-dimensional reconstructions of the breast also can allow for 2D or 3D projection images of the acoustical parameters such that a direct comparison to mammography can be made. In an embodiment, as shown in FIGS. 7A-7D, maximum intensity projections of graphical sound speed maps are shown such that exemplar images of the four BI-RADS categorizes are represented. As seen in FIG. 7A, for example, a sound speed map of a BI-RADS 1/fatty tissue, T, is shown. As seen in FIG. 7B, for example, a sound speed map of a BI-RADS2/scattered tissue, T, is shown. As seen in FIG. 7C, for example, a sound speed map of a BI-RADs 3/heterogeneous tissue, T, is shown. As seen in FIG. 7D, for example, a sound speed map of a BI-RADS 4/dense tissue, T, is shown. Here, the white regions demonstrate high sound speed values relative to the darker lower sound speed regions. It will be appreciated, however, that although maximum intensity projections of three-dimensional sound speed reconstruction is provided in each of FIGS. 7A-7D, graphical representations may be extended to different projections and acoustical parameters other than sound speed.

In an embodiment, the sound speed may be estimated either through direct measurement (e.g., with a transducer pair or set of ultrasound calipers). The direct measurement of sound speed through the tissue, T, is independent of reconstructed images such that the sound speed is determined directly from the timing of the arrival of the pulses without requiring the complexity of any imaging. In another embodiment, a series of sound speed tomographic images can be formed and used to obtain the volume averaged sound speed.

According to an embodiment, the stored data may be analyzed by a software program that is stored, in an embodiment, within the tissue volume separator 48 to determine various acoustic parameters associated with the interaction of the sound waves, U, with the breast tissue, T. The novel methodology associated with the software can be used to categorize breast tissue density and evaluate parameters such as sound speed, attenuation, reflectivity, elasticity, and TDF. It can be appreciated that this software can also be used to provide a combination of such parameters that may best distinguish women with elevated breast density, and, as such, an increased risk of breast cancer. An extension of such software may include the development of a breast cancer risk assessment model to incorporate other risk factors such as age, menopausal status, age at menarche, parity, hormonal usage, age at first birth, number of first and second degree relatives with breast cancer, prior breast biopsies, history of atypical hyperplasia, or history of lobular carcinoma in situ using any number of aforementioned acoustic parameters.

Using aforementioned measurements of the breast, a new classification scheme may be developed to characterize breast density using one or more acoustic parameters, TDF, or any combination thereof. It will be appreciated that due to the multitude of acoustic parameters available and the ability to measure them repeatedly, a more quantitative breast density classification scheme may be realized than currently employed using the mammographic BI-RADS Categories.

Finally, it will be appreciated that many alternative applications to volumetric tissue evaluation over time may be conducted rather than evaluating breast density over time. As noted, a diagnostic value is anticipated from volumetric tissue assessments in response to changes during the exam (e.g., temperature, shape, pressure, intravenous contrasts). Similarly, as seen in FIGS. 8A-8H, malignant tumor responses over time show volume reduction capabilities by utilizing sound speed to analyze the breast tissue, T. In an embodiment, the successive images in FIGS. 8A-8H are taken approximately two weeks apart for a patient undergoing chemotherapy. In an embodiment, changes in sound speed, tumor volume, and other acoustical properties can be tracked and estimated using a tissue volume separator. Accordingly, the invention may be utilized to analyze tumor volume reduction over time as a patient undergoes, for example, chemotherapy, radiation therapy, surgery or the like. In another embodiment, for example in benign tumors and fibrocystic breasts, the effectiveness of dietary and chemoprevention interventions maybe quantifiable in terms of density and acoustic property changes.

5. Benefits of Determining a Breast Density by Utilizing Acoustics

It is known that women under the age of 40 do not routinely undergo mammographic screening for breast cancer because the benefit of receiving mammographic examinations does not outweigh the risk associated with the exposure to ionizing radiation. The processes disclosed herein for determining breast density are conducted without exposing the subject to harmful ionizing radiation, and accordingly allow for risk-free screening and the establishment of baselines at an earlier age. Moreover, the present invention presents and objective approach for assessing present and future cancer risk. This is in contrast to the subjective nature of interpreting mammograms.

Even further, because the tissue undergoing examination, T, is not compressed in any of the methodologies associated with the present invention, the evaluation of the tissue, T, is conducted when the breast tissue is in a non-compressed, natural shape thereby rendering a more accurate representation of the spatial distribution of fibroglandular and fat tissues. Further, by not utilizing a compression technique, women may be more likely to respond favorably to the comfort of the scan, particularly when comparing the embodiments of the present invention to mammography.

In obtaining the breast density by way of the present methodologies, a reduced amount of time may be employed when evaluating a subject's tissue, T; the examination may take as little as five minutes to set-up and one minute to conduct. As a result of knowing one's breast tissue density, preventative measures may be taken, as the relative risk of breast cancer increases with increased breast density. Preventative measures may include, for example, the screening of such subjects at a younger age (e.g., women who are not of mammographic age, such as women that are younger than 40 years old) and/or the screening of such subjects with a greater than annual frequency. In addition, knowing one's tissue density may justify the use of chemoprevention methods. Chemoprevention methods may include, for example, dietary intervention or use of Tamoxifen.

In addition, by knowing one's acoustical or TDF measures, the known tissue density may be utilized as a baseline value for subsequent comparison over time. For example, if a subsequent screening determined breast density has increased in view of one's previous/baseline breast density, the subject may be advised to undergo earlier/preventative screenings, which may not otherwise be suggested without the knowledge of the change in breast density from the baseline.

Volumetric changes over time in response to temporal alterations of the ultrasound parameters provide further potential tissue characterization. Volumetric tissue responses can be measured during a single or multiple scans. Parameters which may be altered during a single scan session may include, but are not limited to: temperature, shape, pressure, and vascular content. Further, it will be appreciated that these more immediate volumetric changes may include all or a portion of the scanned volume. Changes in volumetric ultrasound parameters affecting vascular content may be in response to any variety of intravenous or interstitial agents which change the reflectivity, sound speed, attenuation, elasticity, etc. Volumetric parameters which may be altered during multiple scan session include, but are not limited to, interval interventions, such as: responses to chemotherapy, chemoprevention, dietary changes, radiation treatment, tumor ablations or other surgical interventions.

Even further, it will be appreciated that many alternative applications of the present invention may also be made available. For example, the breast tissue density could be monitored in response to treatments such as, for example, soy isoflavones, dietary interventions, hormone-replacement therapy, and the like. In addition, the acoustical parameters and TDF could evaluate breast density over the phases of one's menstrual cycle, which may assist in determining the ideal time span to evaluate the breast. Alternatively, the breast density could be used to determine the natural variance of breast density for each patient.

The system and/or method of the preferred embodiment and variations thereof can be embodied and/or implemented at least in part as a machine configured to receive a computer-readable medium storing computer-readable instructions. The instructions are preferably executed by computer-executable components preferably integrated with the system 100 and one or more portions of the processor 220. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

We claim:

1. A system for determining present or future cancer risk from a volume of breast tissue, comprising:
    (a) a non-ionizing apparatus comprising a transducer configured to transmit an acoustic signal through the volume of breast tissue;
    (b) a tissue volume separator coupled to the non-ionizing apparatus, wherein the tissue volume separator is configured to facilitate measurement of a distribution of sound speed for the volume of breast tissue based upon an analysis of the acoustic signal; and
    (c) a processor operatively connected to a non-transitory computer-readable storage medium with instructions stored thereon which when executed by the processor are configured to:
        (i) obtain an average whole breast sound speed based on the distribution of sound speed over a volume of the breast,
        (ii) generate a comparison between the average whole breast sound speed and at least one threshold condition associated with breast density of the volume of the breast, wherein the comparison comprises classifying the volume of breast tissue as Breast Imaging Reporting and Data System (BI-RADS) category 4 dense tissue if the average whole breast sound speed is greater than 1476 m/s, and
        (iii) quantify present or future cancer risk based upon the comparison.

2. The system of claim 1, wherein the non-ionizing apparatus comprises a platform disposed substantially adjacent a tank including a coupling fluid, wherein the platform is configured to facilitate insertion of the volume of breast tissue into the tank and proximate to the transducer, and wherein the transducer is configured to transmit the acoustic signal through the breast tissue for receipt at the tissue volume separator.

3. The system of claim 1, wherein the non-ionizing apparatus comprises an ultrasound caliper disposed upon the coupling fluid and proximate to the breast tissue, wherein the ultrasound caliper comprises a transmitting end and a receiving end for transmitting the acoustic signal through the volume of breast tissue for receipt at the tissue volume separator.

4. The system of claim 1, wherein the tissue volume separator comprises an imaging device, a waveform generator, a digital-to-analog converter coupled to the waveform generator, an acoustic transmit amplifier coupled to the digital-to-analog converter, wherein the acoustic transmit amplifier is connected to a transmitter end of the imaging device, a receive amplifier, wherein the receive amplifier is connected to a receiver end of the imaging device, an analog-to-digital converter coupled to the receive amplifier, and a value generator connected to the analog-to-digital converter.

5. The system of claim 4, wherein the imaging device is an ultrasound tomography device defined, at least in part, by a transducer ring configured to scan the volume of breast tissue.

6. The system of claim 1, wherein the at least one threshold condition associated with breast density of the volume of the breast is based at least in part on a threshold value of average whole breast sound speed.

7. A system for determining present or future cancer risk from a volume of breast tissue, comprising:
    (a) a non-ionizing apparatus comprising a transducer configured to transmit an acoustic signal through the volume of breast tissue;
    (b) a tissue volume separator coupled to the non-ionizing apparatus, wherein the tissue volume separator is configured to facilitate measurement of a distribution of sound speed for the volume of breast tissue based upon an analysis of the acoustic signal; and
    (c) a processor operatively connected to a non-transitory computer-readable storage medium with instructions stored thereon which when executed by the processor are configured to:
        (i) obtain an average whole breast sound speed based on the distribution of sound speed over the volume of the breast,
        (ii) generate a comparison between the average whole breast sound speed and at least one threshold condition associated with breast density of the volume of the breast, wherein the comparison comprises classifying the volume of breast tissue as Breast Imaging Reporting and Data System (BI-RADS) category 3 heterogeneous tissue if the average whole breast sound speed has a value from 1463-1476 m/s, and
        (iii) quantify present or future cancer risk based upon the comparison.

8. The system of claim 7, wherein the non-ionizing apparatus comprises a platform disposed substantially adjacent a tank including a coupling fluid, wherein the platform is configured to facilitate insertion of the volume of breast tissue into the tank and proximate to the transducer, and wherein the transducer is configured to transmit the acoustic signal through the breast tissue for receipt at the tissue volume separator.

9. The system of claim 7, wherein the non-ionizing apparatus comprises an ultrasound caliper disposed upon the coupling fluid and proximate to the breast tissue, wherein the ultrasound caliper comprises a transmitting end and a receiving end for transmitting the acoustic signal through the volume of breast tissue for receipt at the tissue volume separator.

10. The system of claim 7, wherein the tissue volume separator comprises an imaging device, a waveform generator, a digital-to-analog converter coupled to the waveform generator, an acoustic transmit amplifier coupled to the digital-to-analog converter, wherein the acoustic transmit amplifier is connected to a transmitter end of the imaging device, a receive amplifier, wherein the receive amplifier is connected to a receiver end of the imaging device, an analog-to-digital converter coupled to the receive amplifier, and a value generator connected to the analog-to-digital converter.

11. The system of claim 10, wherein the imaging device is an ultrasound tomography device defined, at least in part, by a transducer ring configured to scan the volume of breast tissue.

12. The system of claim 7, wherein the at least one threshold condition associated with breast density of the volume of the breast is based at least in part on a threshold value of average whole breast sound speed.

* * * * *